United States Patent [19]
Arav

[11] Patent Number: 6,166,761
[45] Date of Patent: Dec. 26, 2000

[54] METHOD AND APPARATUS FOR MONITORING A BIOLOGICAL SAMPLE

[75] Inventor: Amir Arav, Tel Aviv, Israel

[73] Assignee: Interface Multigrad Technology, Migdal Haemek, Israel

[21] Appl. No.: 08/781,015

[22] Filed: Jan. 9, 1997

[51] Int. Cl.[7] ............................................. H04N 7/18
[52] U.S. Cl. ............................................................ 348/80
[58] Field of Search ................................. 348/42, 46, 47, 348/61, 79, 80

[56] References Cited

U.S. PATENT DOCUMENTS

| | | | |
|---|---|---|---|
| 4,902,132 | 2/1990 | Murphy | 356/339 |
| 5,109,276 | 4/1992 | Nudelman | 348/47 |
| 5,307,161 | 4/1994 | Miyamoto | 348/79 |
| 5,397,709 | 3/1995 | Berndt | 438/34 |
| 5,465,114 | 11/1995 | Miyamoto | 348/80 |
| 5,541,081 | 7/1996 | Hardy | 435/29 |

*Primary Examiner*—Bryan Tung
*Attorney, Agent, or Firm*—Mark M Friedman

[57] ABSTRACT

A method and apparatus for monitoring biological samples. The apparatus comprises an incubator within which are mounted at least two CCD mini-cameras adapted for photomicroscopy as mini-photomicroscopes. The apparatus may be configured for time-lapse photomicroscopy, transmission photomicroscopy, reflection photomicroscopy, epifluorescence photomicroscopy, or infrared photomicroscopy. 3D images are acquired by focusing the mini-photomicroscopes on successive focal image planes in the biological samples. The mini-photomicroscopes may be focused on separate samples, on different portions of the same sample, or on the same portion of the same sample.

2 Claims, 5 Drawing Sheets

METHOD AND APPARATUS FOR MONITORING A BIOLOGICAL SAMPLE

FIELD AND BACKGROUND OF THE INVENTION

The present invention relates to a method for monitoring the development of living biological samples and, more particularly, to an apparatus and method for monitoring the development of incubating cell cultures such as embryos.

Cell cultures commonly are grown inside incubators. An incubator is a closed box within which t he e nvironmental parameters, such as temperature, humidity and atmospheric composition, can be optimized to promote the growth of the cell cultures. For example, mammalian embryos should be incubated under conditions resembling those found inside a mammalian womb.

It is advantageous to monitor the growth of cell cultures using a microscope, so that the details of the development of individual cells may be observed. If a photomicroscope is used, it can be focused on successive focal image planes within the culture, in a manner similar to that taught by Carlsson in U.S. Pat. No. 4,631,581 for microphotometry of prepared biological specimens, to record successive two-dimensional slices through the cell culture, thereby obtaining a three-dimensional record of the structure of the cell culture. Because microscopes are large, bulky, delicate instruments that do not fit inside commonly used incubators, it has been the practice heretofore to enclose microscope stages in specially constructed incubators so that those microscopes could be used to monitor incubating cells. This clearly is an awkward procedure. Furthermore, this procedure allows only one cell culture, or only one portion of a cell culture, to be monitored within the incubator at any given time.

This problem is addressed partially by Miyamoto in U.S. Pat. No. 5,307,161. Miyamoto places a solid-state area image sensor array, such as a charge coupled device (CCD) array, in close proximity to a biological sample within an incubator. CCD arrays are small enough to fit inside commonly used incubators. If positioned close enough to the biological sample, a CCD array does not need an optical system in order to image the sample. Several biological samples may be monitored simultaneously, each by its own CCD array. Signals from the CCD array are transmitted to a display unit such as a video monitor, and also may be digitized, processed and stored in the conventional manner. The drawback of using a solid-state area image sensor array without an optical system, as taught by Miyamoto, is that the resolution of the images obtained is limited by the size of the sensor elements that comprise the array. Sample features smaller than the width of one sensor element cannot be imaged.

There is thus a widely recognized need for, and it would be highly advantageous to have, a method for microscopic monitoring of a living cell culture within a conventional incubator.

SUMMARY OF THE INVENTION

According to the present invention there is provided a method for monitoring the development of a biological sample in an incubator, comprising the steps of: (a) providing, inside the incubator, at least two mini-microscopes, each of the mini-microscopes including: (i) a microscope objective, and (ii) a solid-state area image sensor array, optically coupled to the microscope objective; (b) placing the biological sample in a transparent holder inside the incubator; and (c) focusing each of the at least two mini-microscopes on a focal image plane, at a focal distance from the mini-microscope, in the biological sample.

According to the present invention there is provided an apparatus for monitoring the development of a biological sample, comprising: (a) an incubator; (b) a transparent holder mounted within the incubator; and (c) at least two mini-microscopes, mounted relative to the transparent holder within the incubator so that, when the biological sample is placed in the transparent holder, each of the at least two mini-microscopes may be focused on a focal image plane within the biological sample.

The present invention is made possible by a newly available type of camera, that uses a CCD array instead of photographic film as its light-sensitive element. Such "CCD mini-cameras" are manufactured, for example, by Aplitec Ltd. of Holon, Israel. These cameras are small enough to fit comfortably inside conventional incubators. FIG. 1A is a schematic cross section through a CCD mini-camera 10, showing the parts of the camera that are relevant to the present invention. A housing 12 is provided with an optical system 14 for focusing light on a CCD array 16 enclosed by housing 12. Optical system 14 may be removed and replaced by a different optical system, depending on the use to which camera 10 is to be put. In particular, optical system may be replaced, as shown in FIG. 1B, by an adapter 22 and a conventional microscope objective 24. Adapter 22 is configured to position objective 24 at a distance from CCD array 16 at which a magnified image of an object immediately in front of objective 24 is focused on CCD array 16. This converts CCD mini-camera 10 into a CCD mini-photomicroscope 20. For reference below, the optical axis of mini-photomicroscope 20 is designated by the reference numeral 26. Although mini-photomicroscope 20 is shown configured with CCD array 16, the scope of the present invention includes mini-photomicroscopes configured with any suitable solid-state area image sensor array.

Mini-photomicroscope 20 is small enough so that several mini-photomicroscopes 20 may be mounted inside a conventional incubator. The various configurations in which mini-photomicroscopes 20 may be mounted within an incubator, and used to monitor the development of biological samples such as cell cultures, are discussed below.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and apparatus for monitoring the development of incubated biological samples. Specifically, the present invention can be used to monitor the development of incubated cell cultures such as embryos.

The principles and operation of incubator miniphotomicroscopy according to the present invention may be better understood with reference to the drawings and the accompanying description.

Figure 2:
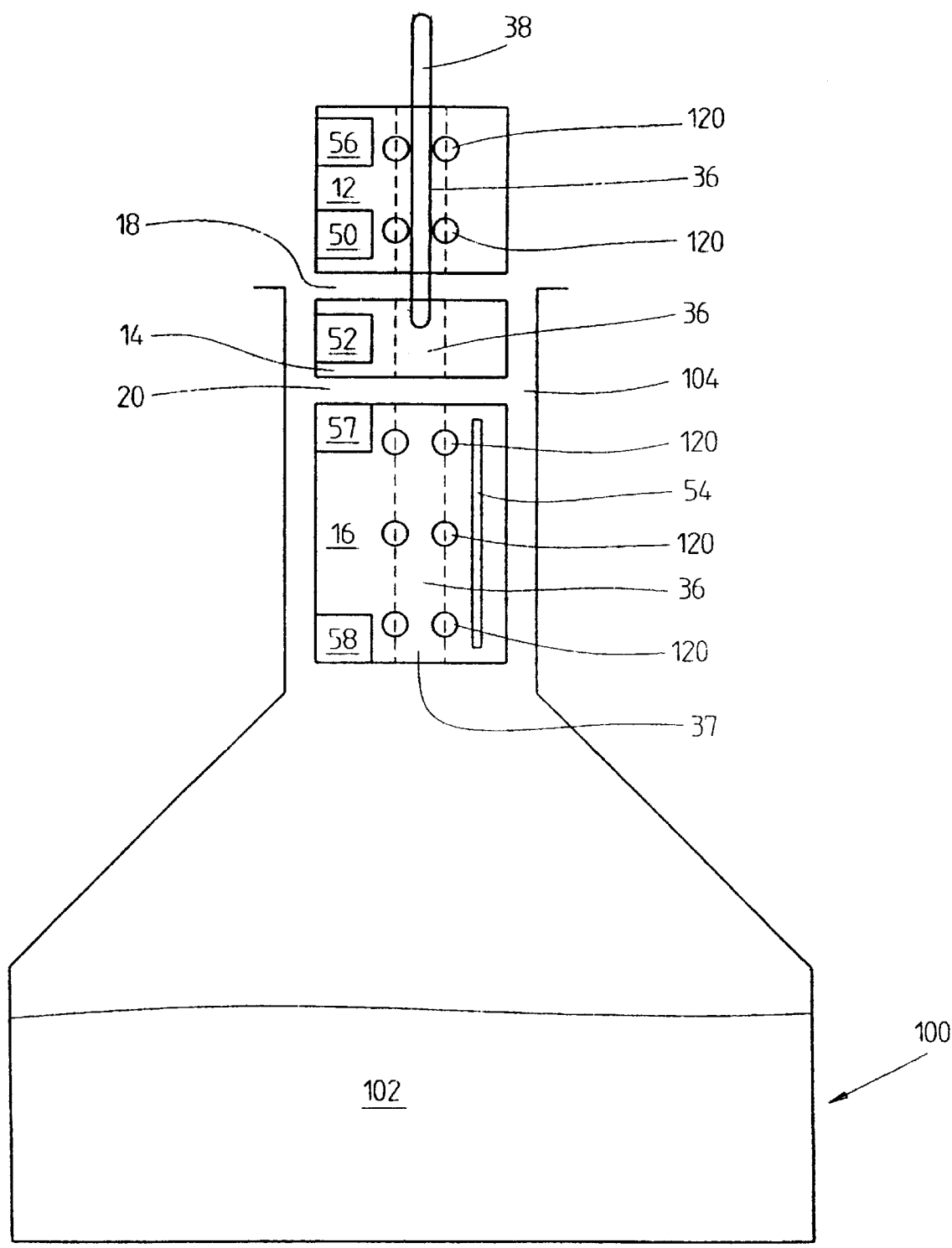
FIG. 2 is a schematic diagram of an incubator system provided with two of the mini-photomicroscopes of FIG. 1B, for monitoring biological samples in Petri dishes.

Referring now to the drawings, FIG. 2 is a schematic diagram of one embodiment of an apparatus for monitoring the development of a biological sample, according to the present invention. The apparatus comprises an incubator 30, within which transparent holders for biological samples, in this case two Petri dishes 34, are placed above holes 33 in a shelf 32. Below Petri dishes 34 are two mini-photomicroscopes 20, mounted on mountings 40. Mountings 40 include step motors 44 that move mini-photomicroscopes 20 up and down to focus, from different focal distances, on different focal imaging planes within the biological samples in Petri dishes 34. For simplicity, FIG. 2 shows only two mini-photomicroscopes 20; the preferred embodiment of the apparatus includes at least four mini-photomicroscopes. Furthermnore, although FIG. 2 shows each of mini-photomicroscopes 20 mounted below a different Petri dish 34, the scope of the present invention includes configurations in which several mini-photomicroscopes are mounted below the same transparent holder, with each mini-photomicroscope monitoring the development of a different biological sample in the transparent holder, or, alternatively, with each mini-photomicroscope monitoring a different portion of the same biological sample.

Light from a light source 50 is directed at Petri dishes 34 from above by optic fiber cables 52, so that mini-photomicroscopes 20 capture images of the biological samples in Petri dishes 34 by transmitted light. Light source 50 and stepping motors 44 are controlled by a control system 60, which is connected to light source 50 and stepping motors 44 by suitable electrical connections 62, such as coaxial cables. Similar connections 64 are used to convey signals from the solid-state area image sensor arrays of mini-photomicroscopes 20 to control system 60. The signals may be digitized, and the corresponding digital images may be displayed on a monitor equipped with an image splitter, or may be recorded for further image processing, by conventional means. Preferably, successive time-lapse images from all mini-photomicroscopes 20 are recorded together on the same recording medium, for example video tape, by the same recording device.

Preferably, control system 60 directs stepping motors to move miniphotomicroscopes 20 up and down continuously, over an appropriate range of distances, to focus continuously on different focal imaging planes within the biological samples. In this way, time lapse 3D images of the biological samples may be acquired, in the manner of Carlsson, and features that move vertically over time within the biological samples may be monitored.

The means for controlling the environmental parameters such as temperature, humidity and atmospheric composition within incubator 30 are conventional, and therefore are not shown in FIG. 2.

The apparatus of FIG. 2 may be used to conveniently monitor the development of mammalian embryos in an environment that simulates the conditions, including total darkness, inside a mammalian womb. For this purpose, incubator 30 is covered with an opaque material, to exclude all light. Light source 50 is turned on periodically, only long enough to capture images of the embryos from the solid-state area image sensors of mini-photomicroscopes 20. While light source 50 is on, mini-photomicroscopes 20 may be moved up and down to focus, from different focal distances, on different focal image planes in the embryos, as described above. Light source 50 may be turned on at regular intervals of on the order of several hours, thereby providing another implementation of time-lapse photomicroscopy of the embryos.

Figure 3:
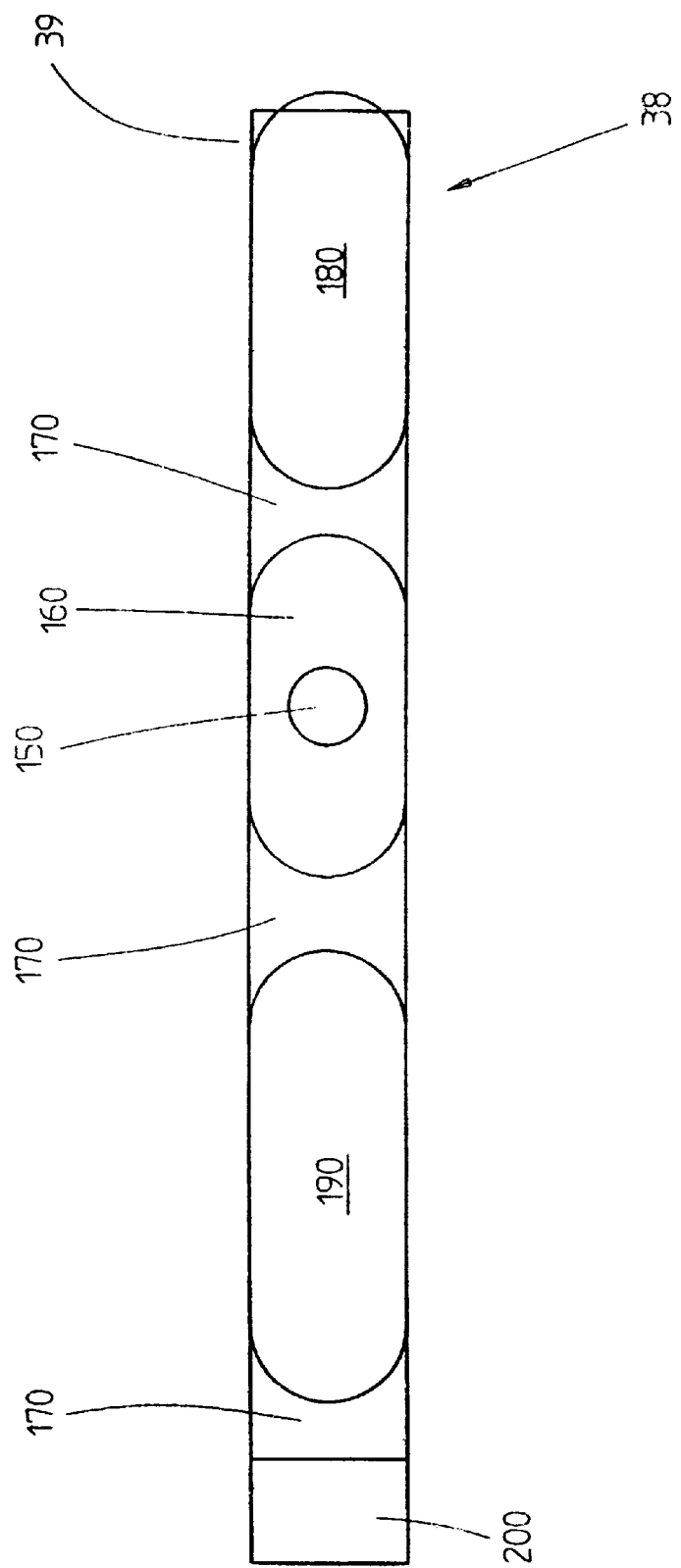
FIG. 3 is a schematic diagram of two of the mini-photomicroscopes of FIG. 1B, deployed at right angles to monitor a biological sample in a square capillary tube.

Most preferably, the solid-state area image sensor arrays of mini-photomicroscopes 20 are long integration time CCD arrays, because of their ability to acquire images at very low levels of light intensities. If these sensitive detectors are used, optic fiber cables 52 may be dispensed with, and a light source 50 of sufficiently low intensity not to disturb the embryos may be located outside incubator 30 but within the opaque material FIG. 3 shows an alternative configuration of mini-photomicroscopes 20 within an incubator 30. In this case, the transparent holder of the biological sample is a capillary tube 36 of square cross section, seen end-on in FIG. 3. Mini-photomicroscopes 20 are focused on the same point in the biological sample, the intersection point 27 of optical axes 26 of mini-photomicroscopes 20. As in the configuration of FIG. 2, fiber optic cables 52 are provided for shining light into capillary tube 36 from the sides opposite mini-photomicroscopes 20. For simplicity, neither mountings 40 nor the means for holding capillary tube 36 are shown in FIG. 3. In the example of FIG. 3, optical axes 26 intersect at a right angle. However, the scope of the present invention also includes capillary tubes of any suitable polygonal cross section: to minimize optical distortion, mini-photomicroscopes 20 are mounted with respect to the capillary tube so that optical axes 26 are perpendicular to the walls of the capillary tube, optical axes 26 then intersecting at whatever angle corresponds to that geometric arrangement.

Figure 1A:
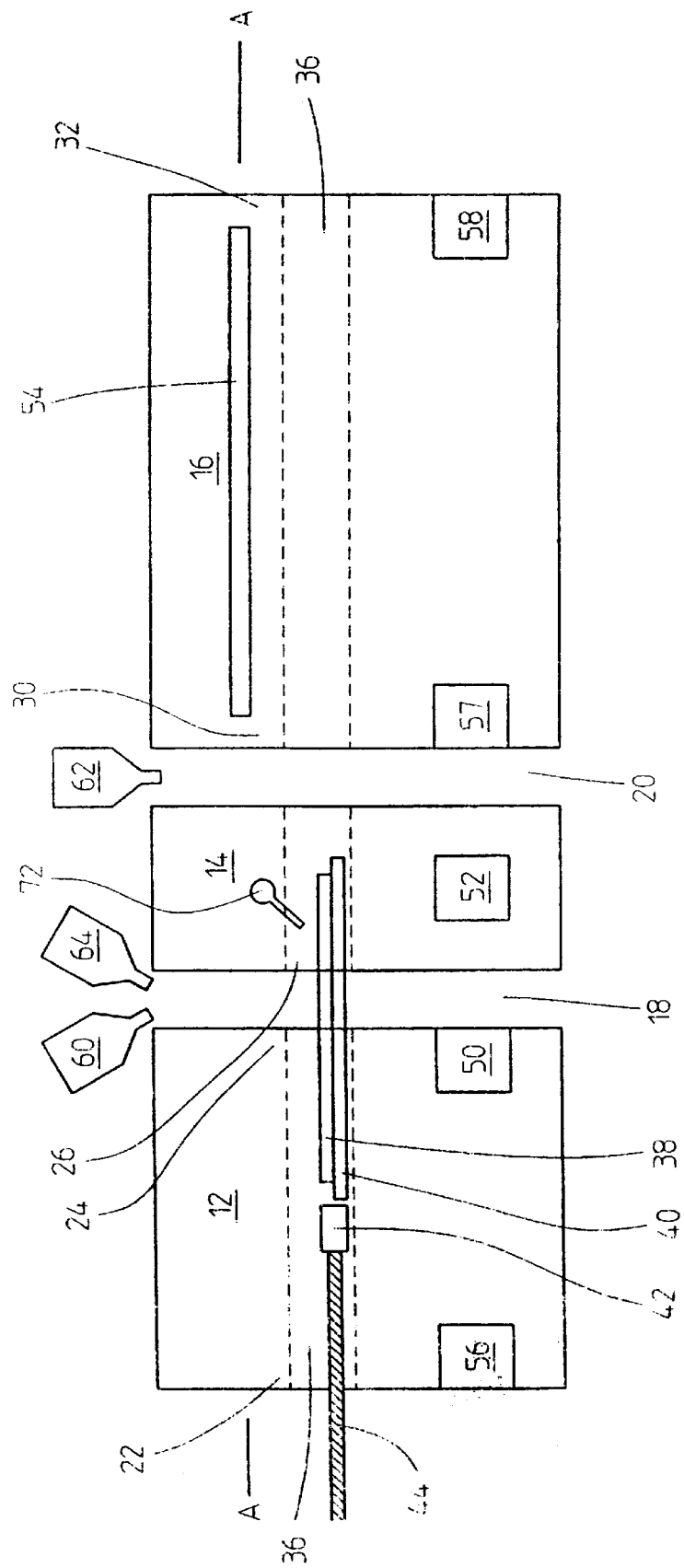
FIG. 1A (prior art) is a schematic cross-section of a CCD mini-camera.
Figure 1B:
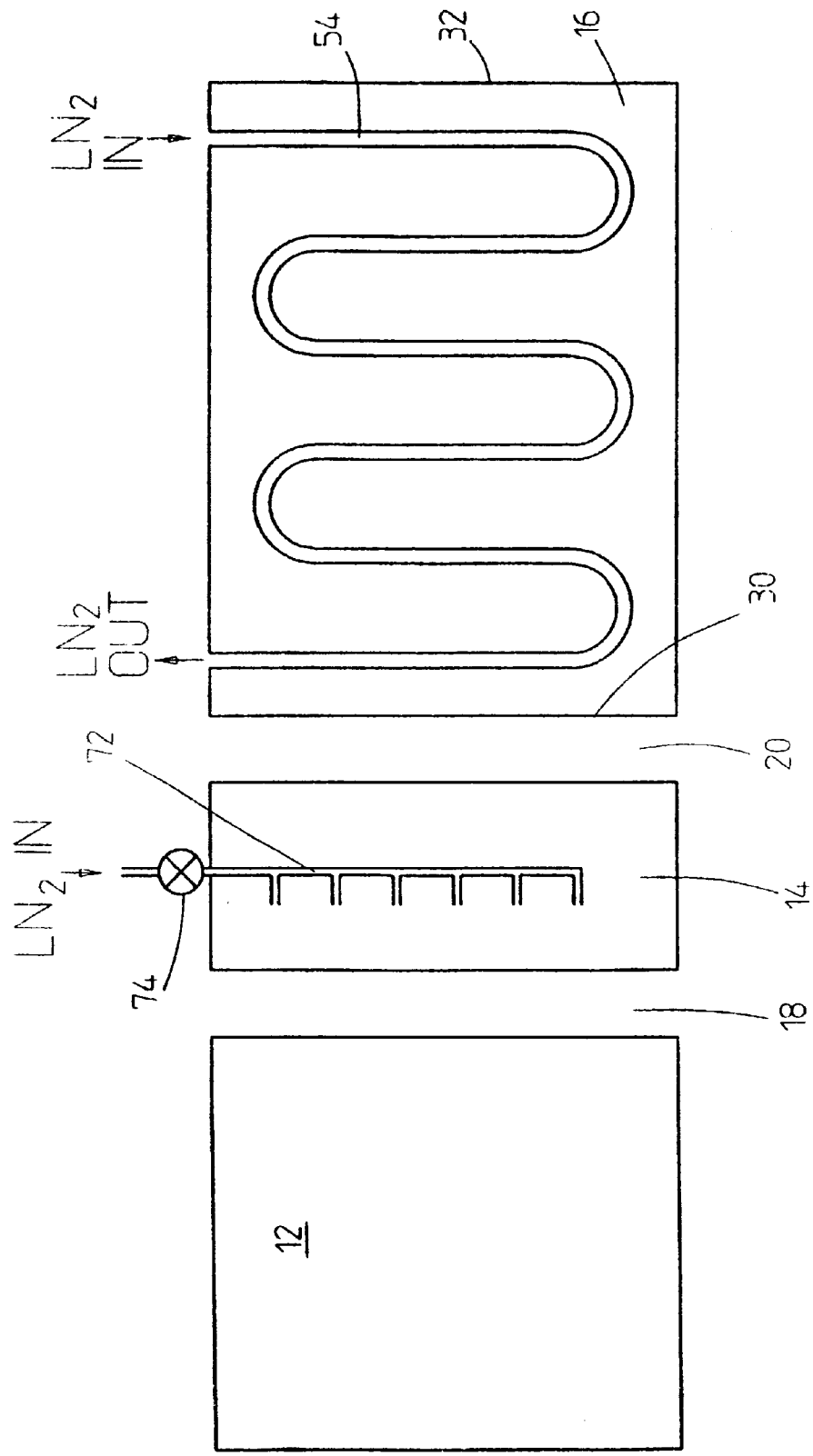
FIG. 1B is a schematic cross-section of the mini-camera of FIG. 1A reconfigured as a mini-photomicroscope.
Figure 4:
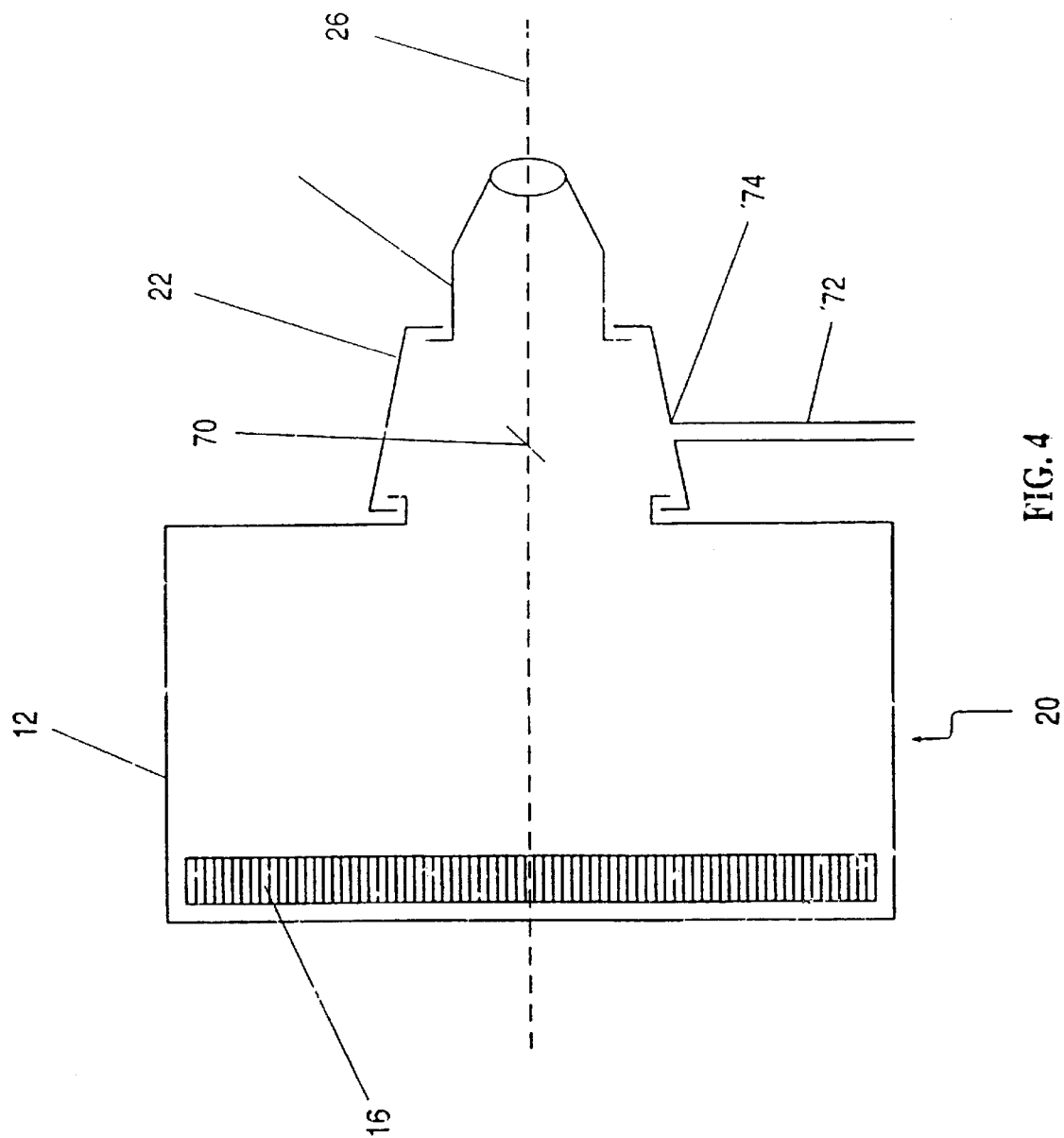
FIG. 4 is an alternative configuration of the mini-photomicroscope of FIG. 1B.

FIG. 4 is a schematic diagram of an alternative embodiment of the mini-photomicroscope of FIG. 1B. In mini-photomicroscope 20' of FIG. 4, adapter 22 is provided with a mirror 70 intersected by optical axis 26, and a port 74 through which light is directed at mirror 70, for example via a fiber optic cable 72. This light is reflected by mirror 70 through the lens of objective 24, and thereby focused on a focal image plane in a biological sample. If the light introduced via fiber optic cable 72 is visible light, this configuration enables reflection photomicroscopy. If the light introduced via fiber optic cable 72 is ultraviolet light, this configuration enables epifluorescence microscopy. If the light introduced via fiber optic cable 72 is infrared light, this configuration enables infrared microscopy, particularly Fourier Transform infrared microscopy.

While the invention has been described with respect to a limited number of embodiments, it will be appreciated that many variations, modifications and other applications of the invention may be made.

What is claimed is:

1. A method for monitoring the development of a biological sample in an incubator, comprising the steps of:
   (a) providing, inside the incubator, at least two mini-photomicroscopes, each of said mini-photomicroscopes including:
      (i) a microscope objective, and
      (ii) a solid-state area image sensor array, optically coupled to said microscope objective;
   (b) placing the biological sample in a transparent holder inside the incubator;

(c) focusing each of said at least two mini-photomicroscopes on a focal image plane in the biological sample; and (d) for at least one of said at least two mini-photomicroscopes, directing and focusing incident radiation through said microscope objective on said focal image plane.

2. An apparatus for monitoring the development of a biological sample, comprising:

(a) an incubator;

(b) a transparent holder mounted within said incubator; and (c) at least two mini-photomicroscopes, mounted relative to said transparent holder within said incubator so that, when the biological sample is placed in the transparent holder, each of said at least two mini-photomicroscopes may be focused on a focal image plane within the biological sample; and (d) for at least one of said at least two mini-photomicroscopes, a mechanism for directing and focusing incident radiation through said microscope objective on said focal image plane.

* * * * *